United States Patent
Miyazaki et al.

(10) Patent No.: US 6,825,259 B2
(45) Date of Patent: Nov. 30, 2004

(54) RESIN-COATED SCALE-LIKE INORGANIC PARTICLES AND COSMETICS WITH THE SAME BLENDED THEREIN

(75) Inventors: Takumi Miyazaki, Kitakyushu (JP); Hirokazu Tanaka, Kitakyushu (JP)

(73) Assignee: Catalysts & Chemicals Industries Co., Ltd., Kawasaki (JP)

( * ) Notice: Subject to any disclaimer, the term of this patent is extended or adjusted under 35 U.S.C. 154(b) by 192 days.

(21) Appl. No.: 10/078,544

(22) Filed: Feb. 21, 2002

(65) Prior Publication Data
US 2003/0171475 A1 Sep. 11, 2003

(51) Int. Cl.$^7$ .................................................. C08K 3/34

(52) U.S. Cl. ...................... 524/449; 524/451; 524/430; 524/404; 523/105

(58) Field of Search ................................. 523/201, 210, 523/205, 216, 171; 524/430, 449, 451, 404, 428, 423

(56) References Cited

U.S. PATENT DOCUMENTS

| | | | | | |
|---|---|---|---|---|---|
| 3,941,731 | A | * | 3/1976 | Camelon et al. | 523/205 |
| 4,112,036 | A | * | 9/1978 | Woodhams et al. | 264/28 |
| 5,156,677 | A | * | 10/1992 | Carpenter et al. | 106/404 |
| 5,228,912 | A | * | 7/1993 | Herget et al. | 106/505 |
| 5,766,577 | A | * | 6/1998 | Hechavarria | 424/63 |
| 6,582,764 | B2 | * | 6/2003 | Fuller et al. | 427/217 |
| 2003/0091813 | A1 | * | 5/2003 | Fuller et al. | 428/323 |

* cited by examiner

*Primary Examiner*—Katarzyna Wyrozebski
(74) *Attorney, Agent, or Firm*—Manabu Kanesaka

(57) ABSTRACT

The resin-coated scale-like inorganic particles have soft feel, adhesivity to human skin and effective in suppressing excessive luster. The scale-like inorganic particles are those with the surface coated with resin, and are characterized in that the 100% modulus of the resin in the tensile test is in a rage from 50 to 3000 N/cm$^2$. The resin is preferably one or more selected from the group consisting of polyurethane, a styrene-butadiene copolymer, an acrylonitrile-butadiene copolymer, a silicone-based elastomer, and a polyolefin-based elastomer. The resin-coated scale-like inorganic particles are blended in the cosmetics according to the present invention.

10 Claims, No Drawings

RESIN-COATED SCALE-LIKE INORGANIC PARTICLES AND COSMETICS WITH THE SAME BLENDED THEREIN

TECHNICAL FIELD

The present invention relates to scale-like inorganic particles each having the resin-coated surface as well as to cosmetics with the resin-coated scale-like inorganic particles blended therein.

BACKGROUND TECHNOLOGY

Conventionally, the scale-like inorganic particles such as mica, talc, and sericite are blended in makeup cosmetics such as powder foundation. The effects provided by blending the scale-like inorganic particles in such cosmetics include the excellent extendibility on human skin, improved dispersibility of color pigments, and high adhesivity to human skin, all of which are properties indispensable for makeup cosmetics. However, as most of the scale-like inorganic particles are made from inorganic oxides such as silica, alumina, and magnesia, the feel is rather hard. In association with recent progress in the field of pulverization, it has become possible to manufacture the scale-like inorganic particles as flakes with improved feels such as lightness, excellent extendibility, and smoothness, but still the scale-like inorganic particles can not provide soft and moist feels.

On the other hand, just because the scale-like inorganic particles have a scale-like form, the contact area to skin is large, and the adhesivity to the human skin is advantageously higher than that of those having any form other than the scale-like one, but as the particles can not follow extension and shrinkage of skin which occur when an expression of a human face changes, so that, with the particles, it has been impossible to prevent the phenomenon generally called "kinking" in which the particles move on the human skin or separation and drop thereof from the human skin.

Japanese Patent Laid-Open Publication No. HEI 7-291834 proposes the coated pigment with at least a portion of a surface thereof coated with multilayered resin particles with an organic ultraviolet ray absorbent contained in the core material section. However, the resin used in this coated pigment is a (meta)acrylic or a styrene-based one, so that the feel is hard, and although the resin particles are effective in diminishing luster of body colors or pearl colors such as mica when unevenly applied thereon, but the soft feel can not be obtained, and the adhesivity to human skin is not sufficient.

Japanese Patent Laid-Open Publication No. HEI 11-92688 proposes the composite powder comprising flake-like powder such as mica titanium with the surface coated with hollow and spherical powder made from, for instance, styrene-acrylic copolymer resin. Although the flake-like composite can hide defects of human skin and give natural finish, the styrene-acrylic copolymer resin is hard in its feel, so that soft feel can not be obtained and the adhesivity to human skin is not sufficient.

Further Japanese Patent Laid-Open Publication No. HEI 6-32996 proposes the surface-modified pearl-like luster pigment coated with a specific polymer or melamine resin, and describes that the surface-modified pearl-like luster pigment is effective in improving dispensability or solubility in various types of media. However the melamine resin does not have elasticity like rubber, and is not intended to give soft feel to flake-like inorganic particles such as mica.

DISCLOSURE OF THE INVENTION

The present invention was made to solve the problems as described above, and it is an object of the present invention to provide scale-like inorganic particles having soft feel and adhesivity to human skin because of its capability to follow movement of the human skin and also effective in suppressing excessive luster. Further it is another object of the present invention to provide cosmetics which can give soft feel to human skin when applied thereon and is excellent in its adhesivity to the human skin because the scale-like powder is blended therein.

The resin-coated scale-like inorganic particles according to the present invention are those with the surface coated with resin, and are characterized in that the 100% modulus of the resin in the tensile test is in a range from 50 to 3000 $N/cm^2$. The resin is preferably one or more selected from the group consisting of polyurethane, a styrene-butadiene copolymer, an acrylonitrile-butadiene copolymer, a silicone-based elastomer, and a polyolefin-based elastomer.

The resin-coated scale-like inorganic particles are blended in the cosmetics according to the present invention.

Therefore the resin-coated scale-like inorganic particles according to the present invention have soft feel and excellent adhesivity to human skin and are effective in suppressing excessive luster. Further the cosmetics according to the present invention have soft feel to human skin when applied thereon and is excellent in its adhesivity to human skin.

BEST MODE FOR CARRYING OUT THE INVENTION

Preferable embodiments of the present invention are described below. At first, the resin-coated scale-like inorganic particles are described. The resin-coated scale-like inorganic particles according to the present invention are those having a resin-coated surface.

1. Scale-Like Inorganic Particles

The scale-like inorganic particles which ay be used in the present invention include natural minerals such as mica, talc, and sericite, synthetic mica, synthetic sericite, plate-formed titanium oxide, plate-formed silica, plate-formed aluminum oxide, boron nitride, barium sulfate, plate-formed titania-silica composite oxide, and bismuth oxychloride. Further, scale-like inorganic particles comprise those described above as a base material and one or more inorganic oxides coating the base material such as titanium oxide, aluminum oxide iron oxide, silicon dioxide, cerium oxide, and zirconium oxide. The scale-like inorganic particles carried organic dye or pigment thereon may be used. Further, one of the various types of scale-like inorganic particles may be used, and also two or more thereof may be used in a mixed form.

An average diameter of the scale-like inorganic particles as described above should preferably be in a range from 1 to 50 $\mu$m, more preferably in a range from 5 to 30 $\mu$m, and most preferably in a range from 6 to 20 $\mu$m. The thickness of the scale-like inorganic particles should preferably be in a range from 0.01 to 1 $\mu$m, and more preferably in a range from 0.1 to 0.5 $\mu$m. When the average diameter of the scale-like inorganic particles is less than 1 $\mu$m, the excellent extendibility and improved dispersibility of the scale-like inorganic particles may be lost. When the average diameter of the scale-like inorganic particles is more than 50 $\mu$m, glittering due to the excessive luster may occur, which is not preferable.

2. Resin

The 100% modulus in the tensile test of the resin used in the present invention is required to be in a range from 50 to 3000 N/cm$^2$. When the 100% modulus of the resin is less than 50 N/cm$^2$, adhesivity of the resultant resin-coated scale-like inorganic particles becomes higher, and in that case blocking between the particles easily occurs, which causes coagulation and is not preferable for obtaining the good feels such as excellent extendibility. On the other hand, when the 100% modulus of the resin is over 3000 N/cm$^2$, flexibility of the resin is not enough, and in this case, the effect of giving soft feel and excellent adhesivity to human skin may sometimes be insufficient. The 100% modulus in the tensile test of the resin should preferably be in a range from 100 to 1500 N/cm$^2$, and more preferably in a range from 100 to 1000 N/cm$^2$. In the range from 100 to 1500 N/cm$^2$ or from 100 to 1000 N/cm$^2$, the effects of giving the excellent extendibility, soft feel, and high adhesivity to human skin are shown most remarkably.

When the 100% modulus in the tensile test of the resin is within the ranges described above, there is not specific restriction over the resin, and resins having elasticity like that of rubber including a polyurethane, a styrene-butadiene copolymer, acrylonitril-butadiene copolymer, a modified acrylic acid ester, silicon rubber, natural rubber, a nylon-based elastomer, a polyester-based elastomer, and a polyolefin-based elastomer may be used. Further, these resins may include a functional group such as calboxylic acid, sulfonic acid, amines or derivatives thereof for forming an emulsion, and a so may include a functional group for forming a bridge such as epoxy or calbodiimide.

The method described below is used to measure the 100% modulus in the tensile test described above. At first, the resin is applied by the doctor blade method, the resin is dried to obtain a film with the thickness of 30 μm, and then an H-shaped film piece for testing is cut out from the dried film above. The right and left edges of the H-shaped film piece for testing is pulled in opposite directions at the tensile rate of 20 mm/minute to determine a relation between the extension (cm) and the stress (load (N)/cross section (cm$^2$)). The "100% modulus" is defined by the stress (N/cm$^2$) when the length of the film piece for testing is extended to twice of the original length thereof.

A quantity of the resin to be coated on each of the resin-coated scale-like inorganic particles should preferably be in a range from 0.1/99.9 to 50/50 as measured by the weight ratio of resin to scale-like inorganic particle. More preferably the weight ratio of resin to scale-like inorganic particle should be a range from 0.5/99.5 to 10/90. When the quantity of resin coating the scale-like inorganic particle as measure by the weight ratio of resin to scale-like inorganic particle is less than 0.1/99.9, the quantity of coating resin is too small, so that the effects of coating the scale-like inorganic part does with the resin, namely the effects of giving high adhesivity or soft feel, can not sufficiently be obtained. When the quantity of coating resin as measured by the weight ratio of resin to scale-like inorganic particle is more than 50/50, blocking between the particles easily occur, which disadvantageously lowers the extendibility on skin, although the actual adverse effect differs according to the 100% modulus of the resin used for coating the scale-like inorganic particles.

The resin should preferably be coated homogeneously on a surface of the scale-like inorganic particles. When the resin is not coated homogeneously, the effect of excellent extendibility or strong adhesion to skin or the effect of suppressing luster may be insufficient. From the viewpoint of suppressing luster, the refraction index of the coating resin should preferably be lower than that of the scale-like inorganic particles to be coated with the resin.

3. Method of Producing the Resin-Coated Scale-Like Inorganic Particles

There is no specific restriction over the method of producing the resin-coated scale-like inorganic particles according to the present invention so far as the resin-coated scale-like inorganic particles as described above can be obtained, and for instance, the following method may be used.

(1) A method, in which scale-like inorganic particles are dispersed in resin emulsion or latex, pH of the dispersion liquid is controlled to lower the stability of the particle constituting the resin in the dispersed state, fine particles of the resin are deposited and laminated on a surface of the scale-like inorganic particles, and the deposited scale-like inorganic particles are dried. The pH of the dispersion liquid differs according to the used resin emulsion, but any pH value is allowable provided that the stability of resin component particles in the dispersed state can be lowered. It should be noted that a dispersion liquid obtained by dispersing fine resin powder in water or alcohol can be used instead of the resin emulsion or latex, and further the fine resin powder may be dissolved in a solvent medium such as water, toluene, methyl ethyl ketone, or xylene. The resin as described above may be used as a self-emulsifying type of emulsion in which the resin is dispersed in water, a compulsorily emulsified type of emulsion in which an emulsifying agent is used, or latex, and further the resin may be used as a liquid in which fine powder thereof is dissolved in a solvent.

(2) A method, in which the scale-like inorganic particles are dispersed in a resin emulsion or in latex, and the resin emulsion is sprayed and dried.

(3) A method, in which the scale-like inorganic particles are dispersed in a resin monomer solution or in a dispersant to polymerize the resin monomer and the polymerized resin monomer is coated on the scale-like inorganic particles.

(4) A method, granulized resin powder and the scale-like inorganic particles are mixed together, a physical force is loaded to the resultant mixture to soften and melt the resin composition by the generated frictional heat and the melted resin is coated over the scale-like inorganic particles. As a device for mixing and melting the resin, for instance, the Mechano-Fusion System produced by HOSOKAWA MICRON K.K. may be used advantageously.

After the resin is coated on the scale-like inorganic particles as described above, the resin deposited on the scale-like inorganic particles can be melted by heating the resin.

The cosmetics according to the present invention are described below. The scale-like inorganic particles described above are blended together with various component as described below in the cosmetics according to the present invention. The blending ratio of the resin-coated scale-like inorganic particles in the cosmetics should preferably be in range from 1 to 90 weight %. More preferably, the blending ratio is in a range from 3 to 60 weight %. When the blending ratio is less than 1 weight %, the effects of improving the adhesivity to human skin and suppressing luster of cosmetics can not be obtained, and on the other hand, when the ratio is more than 90 weight %, the coloring performance and the oily feel originally required to cosmetics can not be provided.

The cosmetics according to the present invention include at least one of components selected from the group consisting of oils such as higher aliphatic alcohols, higher aliphatic acids, ester oil, paraffin oil, and wax; alcohols such as ethyl alcohol, propylene glycol, sorbitol, and glycerin; moisturing agents such as mucosaccharides, collagens, PCA salts, and lactates; various types of nonionic, cationic, anionic, or amphoteric surfactants; thickeners such as gum Arabic, xanthan gum, polyviny pyrrolidone, ethyl cellulose, carboxymethyl cellulose, carboxyvinyl polymer, and denatured or not-denatured clay minerals; solvents such as ethyl acetate, acetone, and toluene; inorganic or organic dyes; antioxidants such as BHT, and tocopherol; water; chemicals, ultraviolet ray absorbents; pH buffers; chelating agents; antiseptics; and fragrant materials. Further, at least one of inorganic fillers such as silica, talc, kaolin, mica body colors, and various types of organic resins. The cosmetics according to the present invention can be produced by any method based on the conventional technology, and are used in various forms including powder-like, cake-like, pencil-shaped, stick-like, liquid-phase, and cream-like forms, and more specifically, the cosmetics may be used in any form of foundation, cream, emulsion eye-shadow, basement for making-up, nail enamel, eye liner, mascara, lip stick, pack, and hair cosmetics.

EXAMPLES

Example 1

100 g aqueous dispersion liquid of not-yellowing type of carbonate-based polyurethane resin (produced by DAIICHI KOGYO SEIYAKU K.K.; glass transition temperature: −21° C., 100% modulus in tensile test: 170 N/cm$^2$, resin particle diameter: 0.031 μm, self-emulsifying type, concentration of solid, component: 38 weight %) and 1862 g of mica with the average particle diameter of 13 μm and thickness of 0.25 μm as scale-like inorganic particles were mixed in 7538 g of deionized water to obtain a mixture solution with the polyurethane resin to mica weight ratio of 2/98 and solid component concentration of 20 weight %. This mixture solution was sprayed in dry atmosphere with the temperature of 70° C. and the humidity of 5%, and was then recovered into a vessel cooled down to 10° C. to obtain resin-coated scale-like inorganic particles (A). The resin-coated scale-like inorganic particles (A) were applied to skin of a tested person, and it was determined that the adhesivity to the skin was higher with softer feel as compared to a case where only mica was applied on the skin and also the luster was suppressed.

Example 2

100 g styrene butadiene-based resin latex (produced by NIPPON ZEON K.K.; glass transition temperature: 12° C., 100% modulus in tensile test: 620 N/cm$^2$, resin particle diameter: 0.15 μm, and solid component concentration: 49 weight %) and 1176 g of talk with the average particle diameter of 12 μm and the thickness of 0.31 μm as scale-like inorganic particles were mixed in 2807 g of deionized water to obtain a mixture solution with the styrene-butadiene resin to talc weight ratio of 4/96 and solid component concentration of 30 weight %. This mixture solution was spayed in the dry atmosphere with the temperature of 70° C. and the humidity of 5%, and was heated under the temperature of 90° C. for 24 hours to obtain the resin-coated scale-like inorganic particles (B). The resin-coated scale-like inorganic particles (B) were applied on skin of a tested person, and it was determined that the adhesivity to skin was higher with softer feel as compared to a case where only talc was applied to skin and also the luster was suppressed.

Example 3

100 g of acrylonitrile-butadiene based resin latex (produced by NIPPON ZEON K.K.; glass transition temperature: −21° C., 100% modulus in tensile test: 210 N/cm$^2$, resin particle diameter: 0.05 μm, and solid component concentration: 41 weight %) as resin and 1254 g of sericite as scale-like inorganic particles with the average particle diameter of 9 μm and the thickness of 0.28 μm were mixed in 5246 g of deionized water to obtain a mixture solution with the acrylonitrile-butadiene resin to sericite weight ratio of 5/95 and solid component concentration of 20 weight %. This mixture solution was sprayed in dry atmosphere with the temperature of 70° C. and the humidity of 5% and dried, and then was recovered into a vessel cooled to the temperature of 10° C. to obtain the scale-like inorganic particles (C). When the resin coated scale-like inorganic particles (C) were applied to skin of a tested person, and it was determined that the adhesivity to skin was higher with softer feel as compared to a case where only sericite was applied to skin and the luster was suppressed.

Comparative Example 1

100 g of polybutadiene resin latex (produced by NIPPON ZEON K.K.; glass transition temperature: −50° C. or below, 100% modulus in tensile test: 40 N/cm$^2$, resin particle diameter: 0.30 μm, and solid component concentration: 54 weight %) as resin and 2646 g of mica as scale-like inorganic particles with the average particle diameter of 13 μm and the thickness of 0.25 μm were mixed in 10754 g of deionized water to obtain a mixture solution with the polybutadiene resin mica weight ratio of 2/98 and solid component concentration of 20 weight %. The mixture solution was sprayed in dry atmosphere with the temperature of 70° C. and the humidity of 5%, and then was recovered into a vessel cooled down to 10° C. to obtain the scale-like inorganic particles (D). When the scale-like inorganic particles (D) were applied to skin of a tested person, and it was determined that the extendibility on the skin was not high and the feel was hard.

Comparative Example 2

100 g of acrylate-based resin latex (produced by NIPPON ZEON K.K.; glass transition temperature: 43° C., 100% modulus in tensile test: 3430 N/cm$^2$, resin particle diameter: 0.20 μm, and solid component concentration: 45 weight %) as resin and 2205 g of mica as the scale-like inorganic particles with the average particle diameter of 13 μm and the thickness of 0.25 μm were fixed in 8945 g of deionized water to obtain a mixture solution with the acrylate-based resin to mica weight ratio of 2/98 and solid component concentration of 20 weight %. The mixture solution as sprayed in the dry atmosphere with the temperature of 70oC. and the humidity of 5%, and was recovered into a vessel cooled down to 10oC to obtain the scale-like inorganic particles (E). When the resin-coated scale-like inorganic particles (E) were applied to skin of a tested person, it was determined that the luster was suppressed more as compared to the resin-coated scale-like inorganic particles (A) to (C), but that the feel was not soft but smooth.

Comparative Example 3

500 ml of deionized water was poured into a round-bottomed flask, and then 1 g of emulsifier (produced by ASAHI DENKA K.K.: Adecasoap SE-10N) was added to the water with the solution fully agitated. Then 2 g azobi-sisobutylnitrile dissolved in 300 g of metylmethacrylate was added to the solution and the resultant mixture solution was emulsified with a homomixer. After emulsification, nitrogen gas was filled inside the flask, and after 30 minutes, polymerization was carried out for 10 hours under the temperature of 73° C. to obtain resin particles with the average particle diameter of 1 μm. The 100% modulus of this resin in a tensile test was measured, but the resin was broken into pieces when extended by 20%, so that measurement of the 100% modulus could not be performed.

45 g of the resin described above dispersed in 55 g of deionized water and 2205 g of mice as the scale-like inorganic particles with the average particle diameter of 1 μm and the thickness of 0.25 μm were mixed in 8945 g of deionized water to obtain a mixture solution with the acrylate resin particle to mica weight ration of 2/98 and solid component concentration of 20 weight %. This mixture solution was sprayed in the dry atmosphere with the temperature of 70° C. and the humidity of 5%, dried, and was recovered into a vessel cooled down to 10° C. to obtain the resin-coated scale-like inorganic particles (F). When the resin-coated scale-like inorganic particles (F) were applied on skin of a tested person, it was determined that the luster was suppressed more as compared to the scale-like inorganic particles (A) to C), and that the feel was not soft but smooth.

Comparative Example 4

220 g of mica as the scale-like inorganic particles with the average particle diameter of 13 μm and the thickness of 0.25 μm was suspended in 1320 ml of toluene, 22 g of polyethylene wax (with the weight of 10,000) was added to the suspension, and the resultant suspension was subjected to dry distillation for one hour, cooled, separated, and dried to obtain the resin-coated scale-like inorganic particles (G). When the resin-coated scale-like inorganic particles (G) were applied to skin of a tested person, it was determined that the effect of suppressing luster was lower as compared to the resin-coated scale-like inorganic particles (A) to (C) with the lower adhesivity to human skin, and that the feel was smooth but not soft.

Examples 4 to 6

The powder foundation with the composition as shown below was prepared by using the resin-coated scale-like inorganic particles (A), (B), and (C) obtained in the examples 1 to 3.

| | | | |
|---|---|---|---|
| (1) | Resin-coated scale-like inorganic particles | 15 | |
| (2) | Sericite | 31 | |
| (3) | Mica | 20 | |
| (4) | Talc | 10 | |
| (5) | Titanium oxide pigment | 5 | |
| (6) | Colcothar | 0.4 | |
| (7) | Yellow iron oxide | 1.6 | |
| (8) | Black iron oxide | 0.05 | |
| (9) | Sorbitan fatty acid ester | 2.5 | |
| (10) | Stearyl alcohol | 6.0 | |
| (11) | Lanolin | 5.0 | |
| (12) | Liquid paraffin | 2.0 | |
| (13) | Triethanol amine | 1.0 | |
| (14) | Methylparaben | 0.45 | |
| (15) | Fragrant material | As required | |

At first, the mixture of components (1) o (8) was prepared. Then the components (9) to (15) were mixed together under the temperature of 70° C. with the resultant mixture fully agitated, and the two mixtures prepared separately were mixed together homogeneously. After the resultant mixture was dried and pulverized to homogenize the granularity, the powder foundations (PA), (PB), and (PC) were prepared. Each of the obtained powder foundations was applied to skin of tested persons, and assessment of sensuality such as feel and observation of the luster were performed. The results are shown in Table 1.

Assessment of Sensuality

Assessment of sensuality of the obtained powder foundations was carried out for 20 women. The assessment was performed by applying a small quantity of each powder foundation onto a cheek and rubbing the applied section with a finger to assess the softness and adhesivity.

◎: Assessed good by 15 or more people.
○: Assessed good by 10 to 14 people.
Δ: Assessed good by 5 to 9 people.
X: Assessed good by 0 to 4 people.

Observation of Luster

Luster of the obtained powder foundations was observed by applying each powder foundation onto a cheek. The result was compared to the luster obtained when the powder foundation obtained in Comparative example 5 described below. The results are shown in Table 1.

◎: The luster was substantially suppressed.
○: The luster was suppressed to some extent.
Δ: The luster was suppressed slightly.
X: The luster was not suppressed at all.

Comparative Example 5

Blending 15 weight portions of sericite in place of the 15 weight portions of the resin-coated scale-like inorganic particles (A) obtained in Example 4, namely blending totally 46 weight portions of sericite therein, the powder foundation (PS) was prepared like in Example 4. The obtained powder foundation (PS) was applied onto skin, and the sensuality such as feel was assessed.

Comparative Examples 6 to 9 (C. Examples 6 to 9)

The powder foundations (PD), (PE), (PF), and (PG) were prepared like in Example 4 by blending the resin-coated scale-like resin-coated scale-like inorganic particles (A) obtained in inorganic particles (D), (E), (F), and (G) respectively in place of Example 4. The obtained powder foundations (PD), (E), (PF), and were applied to skin, and assessment for the sensuality such feel was performed like in Example 4. The results are shown in Table 1.

TABLE 1

| | Scale-like inorganic particles | Softness | Adhesivity | Suppression of luster |
|---|---|---|---|---|
| Example 4 | (A) | ◎ | ◎ | ◎ |
| Example 5 | (B) | ◎ | ○ | ◎ |
| Example 6 | (C) | ◎ | ◎ | ◎ |
| C. example 5 | Sericite | X | X | Δ |
| C. example 6 | (D) | ◎ | X | ◎ |
| C. example 7 | (E) | X | X | ◎ |
| C. example 8 | (F) | X | X | ○ |
| C. example 9 | (G) | Δ | X | Δ |

What is claimed is:

1. Flaky inorganic particles with surfaces coated with a resin, wherein the resin has 100% modulus in a tensile test in a range from 100 to 1500 N/cm$^2$, and is a material selected from the group consisting of silicone-based elastomer, and polyolefin-based elastomer, an the flaky inorganic particles are formed of a material selected from the group consisting of mica, talc, sericite, synthetic mica, synthetic sericite, titanium oxide, silica, aluminum oxide, born nitride, barium sulfate, titania-silica composite oxide, and bismuth oxychloride.

2. The flaky inorganic particles according to claim 1, wherein the inorganic particles are formed of a material selected from the group consisting of mica, talc, sericite, synthetic mica, and synthetic sericite.

3. The flaky inorganic particles according to claim 1, wherein a weight ratio of the resin to the flaky inorganic particles is in a range from 0.1/99.9 to 50/50.

4. A cosmetic comprising the flaky inorganic particles according to claim 1 and at least one material for cosmetic.

5. The flaky inorganic particles according to claim 1, wherein said flaky inorganic particles have a thickness from 0.01 to 1.0 μm.

6. The flaky inorganic particles according to claim 1, wherein said resin is directly coated on the flaky inorganic particles.

7. The flaky inorganic particles according to claim 1, wherein said resin has an emulsifying group at an end thereof so that the resin can be emulsified in water before coated on the surfaces of the flaky inorganic particles.

8. The flaky inorganic particles according to claim 1, wherein said resin contains an emulsifier so that the resin can be emulsified in water before coated on the surfaces of the flaky inorganic particles.

9. Flaky inorganic particles with surfaces coated with a resin, wherein the resin has 100% modulus in a tensile test in a range from 100 to 1500 N/cm$^2$, and is a material selected from the group consisting of polyurethane, styrene-butadiene copolymer, acrylonitrile-butadiene copolymer, silicone-based elastomer, and polyolefin-based elastomer, and the flaky inorganic particles are formed of a material selected from the group consisting of mica, talc, sericite, synthetic mica, synthetic sericite, titanium oxide, silica, aluminum oxide, boron nitride, barium sulfate, titania-silica composite oxide, and bismuth oxychloride, wherein an average particle diameter of the inorganic particles is in a range from 1 to 50 μm.

10. A cosmetic comprising the flaky inorganic particles according to claim 9 and at least one material for cosmetic.

* * * * *